US010401625B2

(12) United States Patent
Petrov

(10) Patent No.: US 10,401,625 B2
(45) Date of Patent: Sep. 3, 2019

(54) DETERMINING INTERPUPILLARY DISTANCE AND EYE RELIEF OF A USER WEARING A HEAD-MOUNTED DISPLAY

(71) Applicant: Facebook Technologies, LLC, Menlo Park, CA (US)

(72) Inventor: Yury Anatolievich Petrov, Coto de Caza, CA (US)

(73) Assignee: Facebook Technologies, LLC, Menlo Park, CA (US)

( * ) Notice: Subject to any disclaimer, the term of this patent is extended or adjusted under 35 U.S.C. 154(b) by 182 days.

(21) Appl. No.: 15/391,204

(22) Filed: Dec. 27, 2016

(65) Prior Publication Data

US 2017/0184847 A1    Jun. 29, 2017

Related U.S. Application Data

(60) Provisional application No. 62/271,632, filed on Dec. 28, 2015.

(51) Int. Cl.

| | | |
|---|---|---|
| G02B 27/00 | (2006.01) |
| G02B 27/01 | (2006.01) |
| G06F 3/13 | (2006.01) |
| G06K 9/00 | (2006.01) |
| A61B 3/11 | (2006.01) |
| G06T 7/70 | (2017.01) |
| H04N 5/225 | (2006.01) |

(Continued)

(52) U.S. Cl.
CPC ............ *G02B 27/017* (2013.01); *A61B 3/111* (2013.01); *A61B 3/152* (2013.01); *G06T 7/586* (2017.01); *G06T 7/70* (2017.01); *H04N 5/2256* (2013.01); *G02B 2027/014* (2013.01); *G02B 2027/0138* (2013.01); *G02B 2027/0159* (2013.01); *G02B 2027/0187* (2013.01); *G06T 2207/30201* (2013.01)

(58) Field of Classification Search
CPC .... G02B 27/017; G02B 27/14; G02B 27/187; G02B 27/172; G02B 27/138; G06T 7/70; A61B 3/06; G03B 15/03; G06K 9/006
USPC .......................................................... 348/78
See application file for complete search history.

(56) References Cited

U.S. PATENT DOCUMENTS

2006/0147094 A1 * 7/2006 Yoo ..................... G06K 9/00604
382/117
2009/0153800 A1 * 6/2009 Bassi ....................... A61B 3/06
351/210

(Continued)

*Primary Examiner* — Patricia I Young
(74) *Attorney, Agent, or Firm* — Fenwick & West LLP

(57) ABSTRACT

A virtual reality headset includes multiple illumination sources emitting light towards a user's eye and an image capture device capturing light reflected by the user's eye. The image capture device captures images of light from the illumination sources reflected by the user's corneas when the user looks at a specific location in the virtual reality headset. Based on locations of light having at least a threshold intensity in the captured images, the position of the center of user's eye's pupil is determined in three dimensions and used to determine a distance between the center of user's eye's pupil and a reference point relative to the illumination sources. Distances between centers of pupils of the user's eyes and reference points are used to determine a distance between the centers of the pupils of the user's eyes and a distance from the corneas to an optical system of the headset.

21 Claims, 4 Drawing Sheets

(51) Int. Cl.
 *A61B 3/15* (2006.01)
 *G06T 7/586* (2017.01)

(56) References Cited

U.S. PATENT DOCUMENTS

2013/0050833 A1* 2/2013 Lewis ................ G06K 9/00604
 359/630
2016/0227113 A1* 8/2016 Horesh .................. G03B 15/03

* cited by examiner

DETERMINING INTERPUPILLARY DISTANCE AND EYE RELIEF OF A USER WEARING A HEAD-MOUNTED DISPLAY

CROSS REFERENCE TO RELATED APPLICATIONS

This application claims the benefit of U.S. Provisional Application No. 62/271,632, filed Dec. 28, 2015, which is incorporated by reference in its entirety.

BACKGROUND

The present disclosure generally relates to head-mounted displays (HMDs), and specifically to determining interpupillary distance and/or eye relief of a user wearing a HMD.

HMDs include a display and optics elements that project the image from the display to the eyes of a user wearing the HMD. The image is projected to an "eye box" for each eye of the user, which is a volume of space in which the user's eyes must be located to view the image correctly. Variations in the shapes of human faces present a challenge for designing HMDs. Accordingly, conventional HMDs are designed to accommodate a range of user anatomies, while sacrificing ideal eye box placement for all users. As a result, variations in the interpupillary distance (i.e., the distance between a person's eyes) and the eye relief (i.e., a depth of the user's eyes relative to other facial features of the user, particularly facial features on which the HMD rests) may result in a user experiencing optical distortions caused by one or both eyes being outside the eye box.

SUMMARY

A virtual reality (VR) system environment includes a system that determines the interpupillary distance between centers of a user's pupils and/or the depth of the user's eyes relative to other facial features of the user (also referred to as "eye relief"). The system may be included in a headset of the VR system including an electronic display presenting content to a user. In various embodiments, the system includes two or more illumination sources and an image capture device, such as a camera. The illumination sources emit light having particular wavelengths and the image capture device is configured to capture light having the particular wavelengths in various embodiments. For example, the illumination sources emit infrared light and the image capture device is configured to capture infrared light. The illumination sources are positioned in the headset to emit light illuminating the surface of a user's eye, and the image capture device captures images of light from the illumination sources reflected by the surface of the user's eye. Hence, the image capture device captures images of light emitted from the illumination sources that is reflected by the cornea of the user's eye.

During a calibration process, the VR system environment prompts the user to look at a particular position of the electronic display and the image capture device captures images of light from the illumination sources reflected by the cornea of the user's eye. The VR system environment determines locations of light having at least a threshold intensity in the captured images of light from the illumination sources reflected by the user's eye. For example, if the illumination sources are positioned as circle, the system determines a circle of locations of light having greater than the threshold intensity in the captured images. Based on the locations of the light having at least the threshold intensity in the captured images, the VR system environment determines a center of the pupil of the user's eye. For example, if the illumination sources are positioned as a circle, the VR system environment determines a circle of light having at least the threshold intensity from the captured images and determines the origin of the determined circle as the pupil of the user's eye. In other embodiments where the illumination sources have different orientations relative to each other, the VR system environment determines the center of the pupil of the user's eye based on the determined locations of light from the illumination sources reflected by the user's eye.

The VR system environment determines a distance between the determined center of the pupil of the user's eye and a reference point of the illumination sources. For example, if the illumination sources are positioned in a circle having an origin at reference point, the VR system environment determines a distance between the reference point and the center of the pupil of the user's eye. Determining distances between the determined center of the pupil of the user's eye and a reference point of the illumination sources for each eye of the user allows the VR system environment to determine an interpupillary distance (IPD) of the user. For example, the VR system environment determines the IPD of the user as a sum of the distance between a reference point of illumination sources for an eye of the user and a reference point of illumination sources for another eye of the user, the distance between the determined center of the pupil of the eye of the user and reference point of illumination sources for an eye of the user, and the distance between the determined center of the pupil of the other eye of the user and reference point of illumination sources for the other eye of the user.

In various embodiments, the VR system environment also determines a distance between the user's eye and a surface of a lens a VR headset including the illumination sources and the image capture device based on one or more dimensions of the determined locations of light from the illumination sources in the captured images. For example, the VR system environment maintains information associating different dimensions of the determined locations of light from the illumination sources in the captured images with different distances between the user's eye and a surface of a lens in the VR headset. For example, if the illumination sources are positioned in a circle having a specified radius from a reference point, the system includes information associating different radii of a circle formed by locations of light from the illumination sources in the captured images with different distances between the user's eye and the surface of the lens in the VR headset. In various embodiments, distances between the user's eye and a surface of the lens in the VR headset 105 corresponding to one or more dimensions of the determined locations of light from the illumination sources in the captured images are initially determined through a function based on the one or more dimensions and subsequently stored for retrieval by the VR system environment.

In some embodiments, the VR system environment repositions a lens or other component in the VR headset based on the determined IPD. For example, the VR headset includes one or more motors that reposition a lens in the VR headset based on the determined IPD. Alternatively, the VR headset presents instructions to the user for manually repositioning the lens in the VR headset based on the determined IPD.

The figures depict embodiments of the present disclosure for purposes of illustration only. One skilled in the art will readily recognize from the following description that alternative embodiments of the structures and methods illustrated herein may be employed without departing from the principles of the disclosure described herein.

DETAILED DESCRIPTION

System Overview

Figure 1:
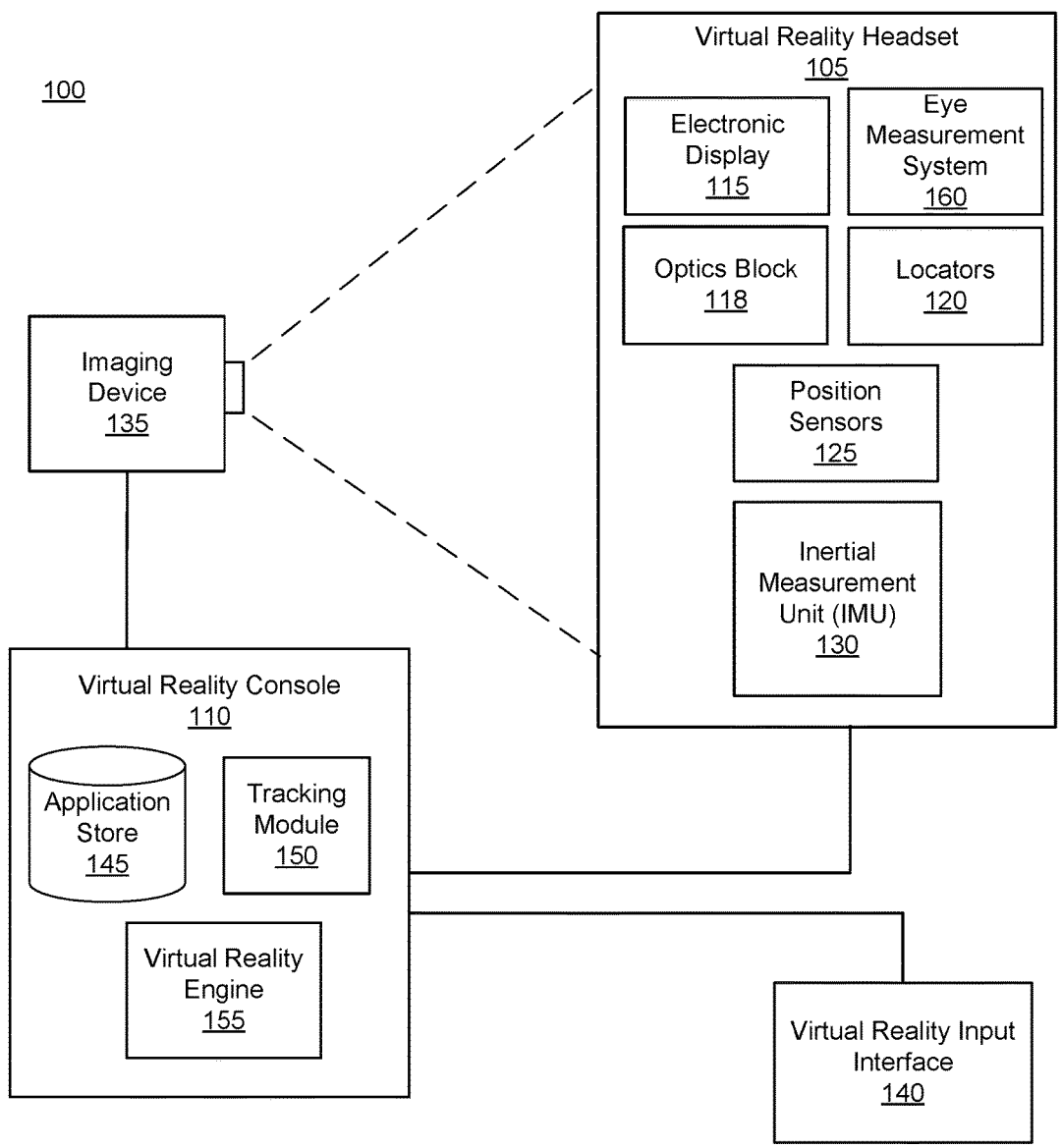
FIG. 1 is a block diagram of a system environment including a virtual reality system, in accordance with an embodiment.

FIG. 1 is a block diagram of a virtual reality (VR) system environment 100 in which a VR console 110 operates. The system environment 100 shown by FIG. 1 comprises a VR headset 105, an image capture device 135, and a VR input interface 140 that are each coupled to the VR console 110. While FIG. 1 shows an example system 100 including one VR headset 105, one image capture device 135, and one VR input interface 140, in other embodiments any number of these components may be included in the system 100. For example, there may be multiple VR headsets 105 each having an associated VR input interface 140 and being monitored by one or more image capture devices 135, with each VR headset 105, VR input interface 140, and image capture devices 135 communicating with the VR console 110. In alternative configurations, different and/or additional components may be included in the VR system environment 100. Additionally, the VR system environment 100 described herein may be an augmented reality system that presents a user with a combination of virtual content and content from an environment surrounding the user.

The VR headset 105 is a head-mounted display (HMD) that presents media to a user. Examples of media presented by the VR head set include one or more images, video, audio, or some combination thereof. In some embodiments, audio is presented via an external device (e.g., speakers and/or headphones) that receives audio information from the VR headset 105, the VR console 110, or both, and presents audio data based on the audio information. An embodiment of the VR headset 105 is further described below in conjunction with FIGS. 2A and 2B. The VR headset 105 may comprise one or more rigid bodies, which may be rigidly or non-rigidly coupled to each other together. A rigid coupling between rigid bodies causes the coupled rigid bodies to act as a single rigid entity. In contrast, a non-rigid coupling between rigid bodies allows the rigid bodies to move relative to each other.

The VR headset 105 includes an electronic display 115, an optics block 118, one or more locators 120, one or more position sensors 125, an inertial measurement unit (IMU) 130, and an eye measurement system 160. The electronic display 115 displays images to the user in accordance with data received from the VR console 110. In various embodiments, the electronic display 115 may comprise a single electronic display or multiple electronic displays (e.g., a display for each eye of a user). Examples of the electronic display 115 include: a liquid crystal display (LCD), an organic light emitting diode (OLED) display, an active-matrix organic light-emitting diode display (AMOLED), some other display, or some combination thereof.

The optics block 118 magnifies received light, corrects optical errors associated with the image light, and presents the corrected image light is presented to a user of the VR headset 105. An optical element may be an aperture, a Fresnel lens, a convex lens, a concave lens, a filter, or any other suitable optical element that affects the blurred image light. Moreover, the optics block 118 may include combinations of different optical elements. In some embodiments, one or more of the optical elements in the optics block 118 may have one or more coatings, such as anti-reflective coatings.

Magnification of the image light by the optics block 118 allows the electronic display 115 to be physically smaller, weigh less, and consume less power than larger displays. Additionally, magnification may increase a field of view of the displayed media. For example, the field of view of the displayed media is such that the displayed media is presented using almost all (e.g., 110 degrees diagonal), and in some cases all, of the user's field of view. Additionally, the optics block 118 may be designed so its effective focal length is larger than the spacing to the electronic display 115, which magnifies the image light projected by the electronic display 115. Additionally, in some embodiments, the amount of magnification may be adjusted by adding or removing optical elements.

The optics block 118 may be designed to correct one or more types of optical error. Examples of optical error include: barrel distortion, pincushion distortion, longitudinal chromatic aberration, transverse chromatic aberration, other types of two-dimensional optical error spherical aberration, comatic aberration, field curvature, astigmatism, or any other type of three-dimensional optical error. In some embodiments, content provided to the electronic display 115 for display is pre-distorted, and the optics block 118 corrects the distortion when is receives image light from the electronic display 115 generated based on the content.

The locators 120 are objects located in specific positions on the VR headset 105 relative to one another and relative to a specific reference point on the VR headset 105. A locator 120 may be a light emitting diode (LED), a corner cube reflector, a reflective marker, a type of light source that contrasts with an environment in which the VR headset 105 operates, or some combination thereof. In embodiments where the locators 120 are active (i.e., an LED or other type of light emitting device), the locators 120 may emit light in the visible band (~380 nm to 750 nm), in the infrared (IR) band (~750 nm to 1 mm), in the ultraviolet band (10 nm to 380 nm), some other portion of the electromagnetic spectrum, or some combination thereof.

In some embodiments, the locators 120 are located beneath an outer surface of the VR headset 105, which is transparent to the wavelengths of light emitted or reflected by the locators 120 or is thin enough to not substantially attenuate the wavelengths of light emitted or reflected by the locators 120. Additionally, in some embodiments, the outer surface or other portions of the VR headset 105 are opaque in the visible band of wavelengths of light. Thus, the locators 120 may emit light in the IR band under an outer surface that is transparent in the IR band but opaque in the visible band.

The IMU 130 is an electronic device that generates fast calibration data based on measurement signals received from one or more of the position sensors 125. A position sensor 125 generates one or more measurement signals in response to motion of the VR headset 105. Examples of position sensors 125 include: one or more accelerometers, one or more gyroscopes, one or more magnetometers, another suitable type of sensor that detects motion, a type of sensor used for error correction of the IMU 130, or some combination thereof. The position sensors 125 may be located external to the IMU 130, internal to the IMU 130, or some combination thereof.

Based on the one or more measurement signals from one or more position sensors 125, the IMU 130 generates fast calibration data indicating an estimated position of the VR headset 105 relative to an initial position of the VR headset 105. For example, the position sensors 125 include multiple accelerometers to measure translational motion (forward/back, up/down, left/right) and multiple gyroscopes to measure rotational motion (e.g., pitch, yaw, roll). In some embodiments, the IMU 130 rapidly samples the measurement signals and calculates the estimated position of the VR headset 105 from the sampled data. For example, the IMU 130 integrates the measurement signals received from the accelerometers over time to estimate a velocity vector and integrates the velocity vector over time to determine an estimated position of a reference point on the VR headset 105. Alternatively, the IMU 130 provides the sampled measurement signals to the VR console 110, which determines the fast calibration data. The reference point is a point that may be used to describe the position of the VR headset 105. While the reference point may generally be defined as a point in space; however, in practice the reference point is defined as a point within the VR headset 105 (e.g., a center of the IMU 130).

The IMU 130 receives one or more calibration parameters from the VR console 110. As further discussed below, the one or more calibration parameters are used to maintain tracking of the VR headset 105. Based on a received calibration parameter, the IMU 130 may adjust one or more IMU parameters (e.g., sample rate). In some embodiments, certain calibration parameters cause the IMU 130 to update an initial position of the reference point so it corresponds to a next calibrated position of the reference point. Updating the initial position of the reference point as the next calibrated position of the reference point helps reduce accumulated error associated with the determined estimated position. The accumulated error, also referred to as drift error, causes the estimated position of the reference point to "drift" away from the actual position of the reference point over time.

The eye measurement system 160 determines a distance between centers of pupils of a user's eyes (an "interpupillary distance") and may also determine a distance between a portion of the user's eye (e.g., a cornea of the user's eye) and a surface of a lens in the VR headset 105 nearest the user's eye ("eye relief"). As further described below in conjunction with FIGS. 3 and 4, the eye measurement system 160 includes one or more illumination sources that emit light towards the user's eye and an image capture device configured to capture images light from the illumination sources reflected by the user's eye. Based on locations of light having at least a threshold intensity in the images captured by the image capture device, the eye measurement system 160 determines a center of the pupil of the user's eye in three dimensions and determines a distance between the determined center of the pupil of the user's eye and a reference point. In some embodiments, based on dimensions of the locations of light having at least the threshold intensity in the images captured by the image capture device, the eye measurement system 160 determines the distance between a portion of the user's eye (e.g., a cornea of the user's eye) and a surface of a lens in the VR headset 105 nearest the user's eye. Additionally, the eye measurement system 160 may reposition one or more components of the VR headset 105, such as lenses, based on the determined interpupillary distance or based on the determined distance between a portion of the user's eye (e.g., a cornea of the user's eye) and a surface of a lens in the VR headset 105 nearest the user's eye. For example, the eye measurement system 160 includes one or more motors that reposition a lens, or another component of the VR headset 105, based on the interpupillary distance or based on the distance between a portion of the user's eye (e.g., a cornea of the user's eye) and a surface of a lens in the VR headset 105 nearest the user's eye. Alternatively, the eye measurement system 160 prompts the user to manually reposition one or more components of the VR headset based on the interpupillary distance or based on the distance between a portion of the user's eye (e.g., a cornea of the user's eye) and a surface of a lens in the VR headset 105 nearest the user's eye.

The image capture device 135 generates slow calibration data in accordance with calibration parameters received from the VR console 110. Slow calibration data includes one or more images showing observed positions of the locators 120 that are detectable by the image capture device 135. The image capture device 135 may include one or more cameras, one or more video cameras, any other device capable of capturing images including one or more of the locators 120, or some combination thereof. Additionally, the image capture device 135 may include one or more filters (e.g., used to increase signal to noise ratio). The image capture device 135 is configured to detect light emitted or reflected from locators 120 in a field of view of the image capture device 135. In embodiments where the locators 120 include passive elements (e.g., a retroreflector), the image capture device 135 may include a light source that illuminates some or all of the locators 120, which retro-reflect the light towards the light source in the image capture device 135. Slow calibration data is communicated from the image capture device 135 to the VR console 110, and the image capture device 135 receives one or more calibration parameters from the VR console 110 to adjust one or more imaging parameters (e.g., focal length, focus, frame rate, ISO, sensor temperature, shutter speed, aperture, etc.).

The VR input interface 140 is a device that allows a user to send action requests to the VR console 110. An action request is a request to perform a particular action. For example, an action request may be to start or end an application or to perform a particular action within the application. The VR input interface 140 may include one or more input devices. Example input devices include: a keyboard, a mouse, a game controller, or any other suitable device for receiving action requests and communicating the received action requests to the VR console 110. An action request received by the VR input interface 140 is communicated to the VR console 110, which performs an action corresponding to the action request. In some embodiments, the VR input interface 140 may provide haptic feedback to the user in accordance with instructions received from the VR console 110. For example, haptic feedback is provided when an action request is received, or the VR console 110 communicates instructions to the VR input interface 140 causing the VR input interface 140 to generate haptic feedback when the VR console 110 performs an action.

The VR console 110 provides media to the VR headset 105 for presentation to the user in accordance with information received from one or more of: the image capture device 135, the VR headset 105, and the VR input interface 140. In the example shown in FIG. 1, the VR console 110 includes an application store 145, a tracking module 150, and a virtual reality (VR) engine 155. Some embodiments of the VR console 110 have different modules than those described in conjunction with FIG. 1. Similarly, the functions further described below may be distributed among components of the VR console 110 in a different manner than is described here.

The application store 145 stores one or more applications for execution by the VR console 110. An application is a group of instructions, that when executed by a processor, generates content for presentation to the user. Content generated by an application may be in response to inputs received from the user via movement of the HR headset 105 or the VR interface device 140. Examples of applications include: gaming applications, conferencing applications, video playback application, or other suitable applications.

The tracking module 150 calibrates the VR system environment 100 using one or more calibration parameters and may adjust one or more calibration parameters to reduce error in determination of the position of the VR headset 105. For example, the tracking module 150 adjusts the focus of the image capture device 135 to obtain a more accurate position for observed locators on the VR headset 105. Moreover, calibration performed by the tracking module 150 also accounts for information received from the IMU 130. Additionally, if tracking of the VR headset 105 is lost (e.g., the image capture device 135 loses line of sight of at least a threshold number of the locators 120), the tracking module 140 re-calibrates some or all of the VR system environment 100.

The tracking module 150 tracks movements of the VR headset 105 using slow calibration information from the image capture device 135. The tracking module 150 determines positions of a reference point of the VR headset 105 using observed locators from the slow calibration information and a model of the VR headset 105. The tracking module 150 also determines positions of a reference point of the VR headset 105 using position information from the fast calibration information. Additionally, in some embodiments, the tracking module 150 may use portions of the fast calibration information, the slow calibration information, or some combination thereof, to predict a future location of the headset 105. The tracking module 150 provides the estimated or predicted future position of the VR headset 105 to the VR engine 155.

The VR engine 155 executes applications within the system environment 100 and receives position information, acceleration information, velocity information, predicted future positions, or some combination thereof of the VR headset 105 from the tracking module 150. Based on the received information, the VR engine 155 determines content to provide to the VR headset 105 for presentation to the user. For example, if the received information indicates that the user has looked to the left, the VR engine 155 generates content for the VR headset 105 that mirrors the user's movement in a virtual environment. Additionally, the VR engine 155 performs an action within an application executing on the VR console 110 in response to an action request received from the VR input interface 140 and provides feedback to the user that the action was performed. The provided feedback may be visual or audible feedback via the VR headset 105 or haptic feedback via the VR input interface 140.

Figure 2A:
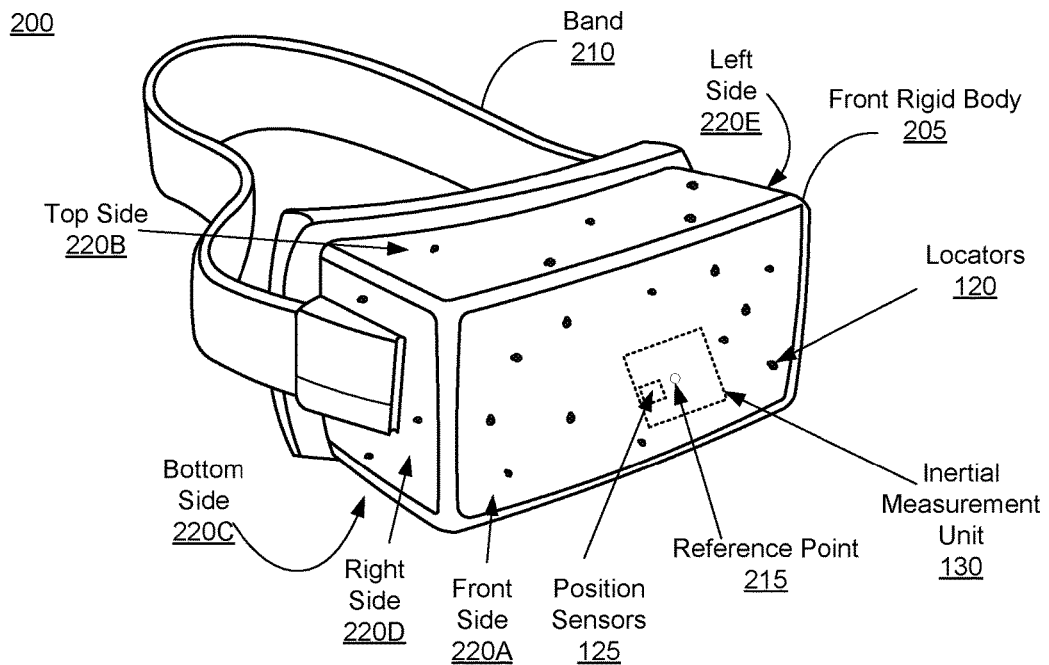
FIG. 2A is a diagram of a virtual reality headset, in accordance with an embodiment.

FIG. 2A is a diagram of one embodiment of the virtual reality (VR) headset 105. The VR headset 200 includes a front rigid body 205 and a band 210. The front rigid body 205 includes the electronic display 115 (not shown in FIG. 2A), the IMU 130 (not shown in FIG. 2A), the one or more position sensors 125 (not shown in FIG. 2A), the locators 120, and the eye measurement system 160. In other embodiments, the VR headset 200 may include different or additional components than those depicted by FIG. 2A.

The locators 120 are located in fixed positions on the front rigid body 205 relative to one another and relative to a reference point. For example, the reference point is located at the center of the IMU 130. Each of the locators 120 emit light that is detectable by the external image capture device 135. Locators 120, or portions of locators 120, are located on a front side 220A, a top side 220B, a bottom side 220C, a right side 220D, and a left side 220E of the front rigid body 205 in the example of FIG. 2A.

Figure 2B:
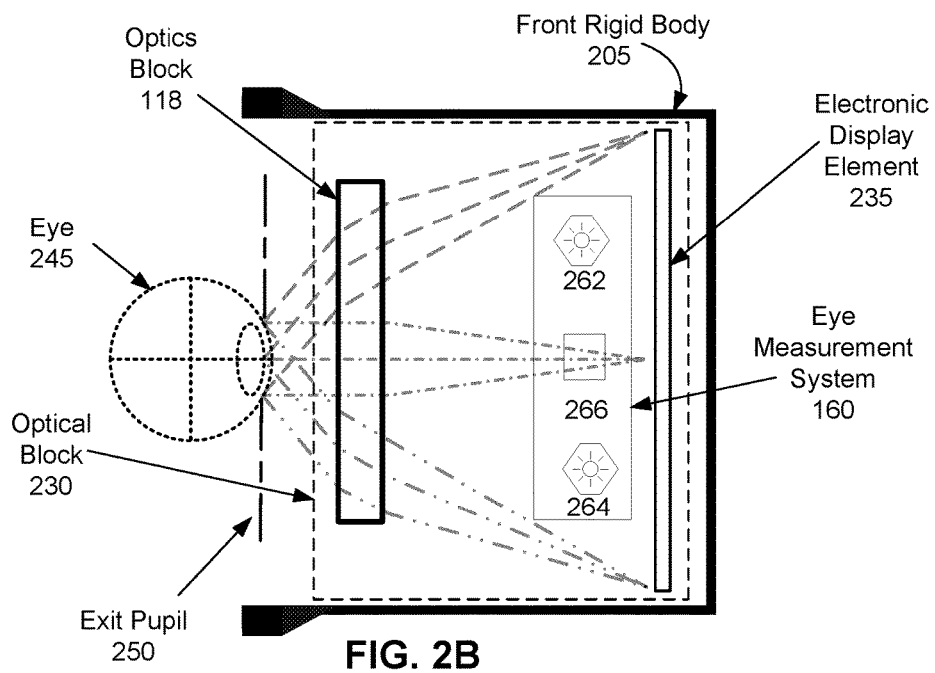
FIG. 2B is a cross section of a front rigid body of the virtual reality headset in FIG. 2A, in accordance with an embodiment.

FIG. 2B is a cross section 225 of the front rigid body 205 of the embodiment of a VR headset 200 shown in FIG. 2A. As shown in FIG. 2B, the front rigid body 205 includes an optical block 230 providing altered image light to an exit pupil 250, which is a location of the front rigid body 205 where a user's eye 245 is positioned. For purposes of illustration, FIG. 2B shows a cross section 225 associated with a single eye 245, but another optical block, separate from the optical block 230, provides altered image light to another eye of the user.

The optical block 230 includes an electronic display element 235 of the electronic display 115, the optics block 118, and an eye measurement system 160. The electronic display element 235 emits image light toward the optics block 118, which magnifies the image light. In some embodiments, the optics block 118 also corrects for one or more optical errors (e.g., distortion, astigmatism, etc.) in the image light. The optics block 118 directs the image light to the exit pupil 250 for presentation to the user.

The VR headset 200 includes an eye measurement system 160 including two or more illumination sources and an image capture device. In the example shown by FIG. 2B, the eye measurement system 160 includes two illumination sources 262 and 264 and an image capture device 266. Another optical block similarly includes an eye measurement system 160 for another eye of the user. The illumination sources 262, 264 and the image capture device 266 are coupled to a control module that receives image data from the image capture device 266 and analyzes the image data to identify characteristics of the user's eye. In some embodiments, the control module is included in the VR headset 200, while in other embodiments, the control module is included in the VR console 110. Alternatively, functionality of the control module is provided by the VR headset 200 and by the VR console 110 in some embodiments.

The illumination sources 262 and 264 are positioned to emit light towards the user's eye, while the image capture device 266 is positioned to capture images of light from the illumination source 262 and 264 reflected by the user's eye, such as light reflected by the cornea of the user's eye. In some embodiments, the eye measurement system 160 is positioned along an axis of the user's vision, such as in the example of FIG. 2B. Alternatively, the eye measurement system 160 is positioned along an axis parallel to the axis of the user's vision. The eye measurement system 160 is further described below in conjunction with FIG. 3.

Eye Measurement System to Determine Interpupillary Distance

Figure 3:
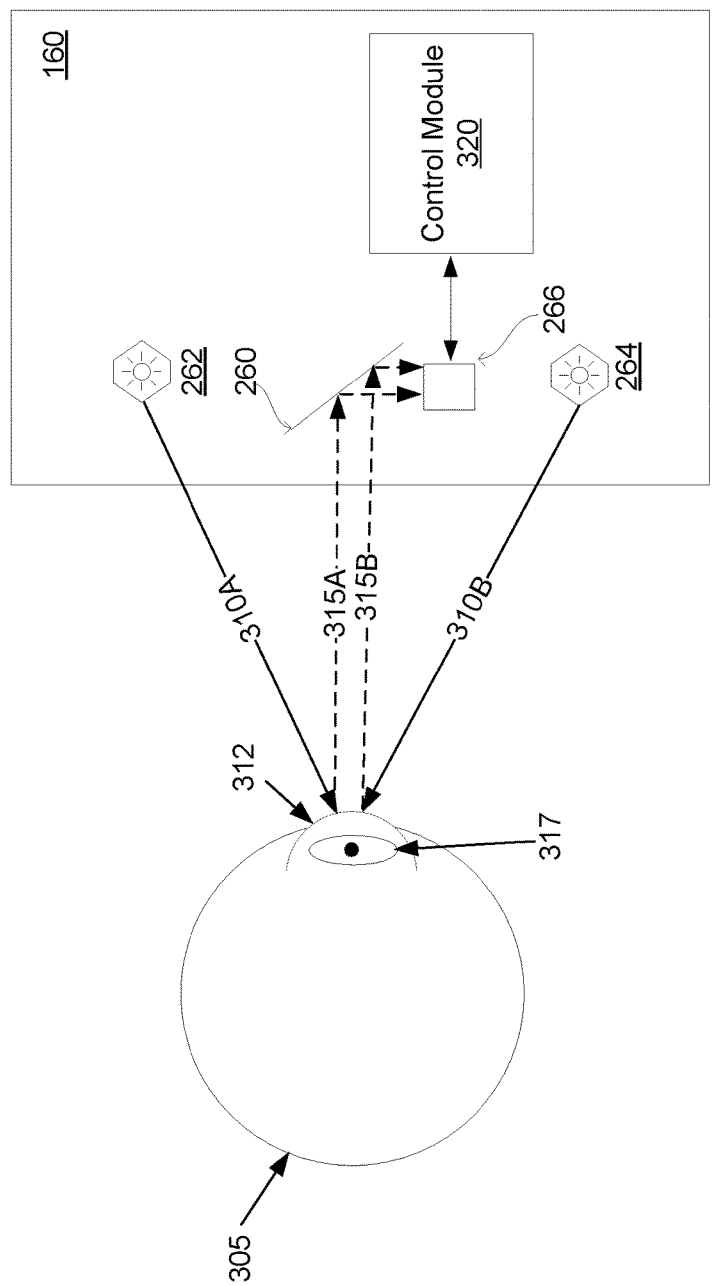
FIG. 3 depicts an example eye measurement system for determining interpupillary distance between centers of pupils of a user's eyes, in accordance with an embodiment.

FIG. 3 is a block diagram of one embodiment of an eye measurement system 160. As described above in conjunction with FIGS. 1-2B, the eye measurement system 160 is included in a VR headset 105 in various embodiments.

However, in other embodiments, the eye measurement system 160 may be included in any other suitable component of a VR system environment 100 or in another system. For purposes of illustration, FIG. 3 shows an eye measurement system 160 for a single eye 305 of a user; however, in various embodiments, a VR headset 105 or other device includes an eye measurement system 160 for each of a user's eyes.

The eye measurement system 160 includes two or more illumination sources 262 and 264 and an image capture device 266, such as a camera. Additionally, a control module 320 is coupled to the image capture device 266 and to the illumination sources 262, 264. In various embodiments, the illumination sources 262, 264 have specified positions relative to each other or relative to a reference point. For example, the illumination sources 262, 264 are positioned in a common two-dimensional plane as a reference point and positioned specific distances from the reference point. In some embodiments, multiple illumination sources 262, 264 are positioned to form a circle with an origin at the reference point and having a specified radius. In one embodiment, the illumination sources 262, 264 are positioned outside of the user's line of sight. Additionally, in some embodiments, illumination sources 262, 264 are positioned in different planes than a plane including the reference point. For example, different illumination sources 262, 264 are positioned at different depths from the reference point. Light from the illumination sources 262, 264 is directed toward a surface of the user's eye, such as a cornea 312 of the user's eye 305.

In some embodiments, various illumination sources 262, 264 emit light having one or more specific wavelengths or specific temporal patterns (e.g., a specific timing pattern when the illumination sources 262, 264 emit and do not emit light). For example, each illumination source 262, 264 emits infrared light. In one embodiment, each illumination source 262, 264 is a light emitting diode (LED) configured to emit light having infrared wavelengths (i.e., infrared light). However, in other embodiments, light emitted from different illumination sources 262, 264 may have different wavelengths. Additionally, light emitted by different illumination sources 262, 264 may have different characteristics. For example, light emitted from different illumination sources 262, 264 may be modulated at different frequencies, may have different amplitudes, or may have differences in any other suitable characteristics.

The image capture device 266 captures images of light from the illumination sources 262, 264 reflected by the user's eye 305. For example, the image capture device 266 is an infrared camera that captures images of infrared light emitted from the illumination sources 262, 264 and reflected by the user's eye 305 (e.g., by the cornea 312 of the user's eye 305). In various embodiments, the image capture device 266 has a high frame rate and high resolution. The image capture device 266 may capture two-dimensional images or three-dimensional images in various embodiments. In various embodiments, a hot mirror 260 is positioned in the eye measurement system 160 to reflect infrared light towards the image capture device 266, while allowing visible light to pass through the hot mirror 260. For example, the hot mirror 260 has a 45 degree angle of incidence and is positioned in a VR headset 105 between the user's eye 305 and the electronic display 115, so infrared light from the one or more illumination sources 262, 264 reflected by the user's eye is reflected by the hot mirror 260 to the image capture device 266, while visible light from the electronic display 115 is not redirected by the hot mirror 260. In other embodiments, the image capture device 266 has any suitable position capable of capturing light from the illumination sources 262, 264 reflected by the user's eye. For example, the image capture device 266 is included in a plane that includes one or more of the illumination sources 262, 264. Multiple image capture devices 266 may be included in the eye measurement system 160 in some embodiments.

In the example of FIG. 3, the illumination source 262 emits infrared light 310A towards the user's eye 305, and a portion of the infrared light 310A is reflected by a surface of the user's eye 305 (e.g., the cornea 312 of the user's eye 305). The reflected infrared light 315A is reflected by the hot mirror 260 to the image capture device 266, which captures one or more images of the reflected infrared light 315A. Similarly, the illumination source 264 emits infrared light 310B towards the user's eye 305, and a portion of the infrared light 310B is reflected by a surface of the user's eye 305 (e.g., the cornea 312 of the user's eye 305). The reflected infrared light 315B is reflected by the hot mirror 260 to the image capture device 266, which captures one or more images of the reflected infrared light 315B. In various embodiments, the reflected infrared light 315A, 315B is reflected by a cornea 312 of the user's eye 305 or from a lens of the user's eye 305.

The control module 320 receives images of the reflected infrared light 315A, 315B captured by the image capture device 320. Based on the received images from the image capture device 320, the control module 320 determines a center 317 of the pupil of the user's eye 305 in three spatial dimensions. The control module 320 determines a distance between pupils of eyes of the user (i.e., an "interpupillary distance" of the user) based on the centers of the pupils of each of a user's eyes. Additionally, the control module 320 may also determine a distance between the user's eye and a surface of a lens in the VR headset 105 nearest to the user's eye based on the received images. Determination of interpupillary distance and the determine a distance between the user's eye and a surface of a lens in the VR headset 105 nearest to the user's eye is further described below in conjunction with FIG. 4. In some embodiments, a single control module 320 is coupled to eye measurement systems 160 for both eyes of the user. Alternatively, different eye measurement systems 160 for each eye of the user are coupled to different control modules 320. The control module 320 may also communicate instructions to the illumination sources 262, 264 that cause the illumination sources 262, 264 to emit light or to stop emitting light.

Figure 4:
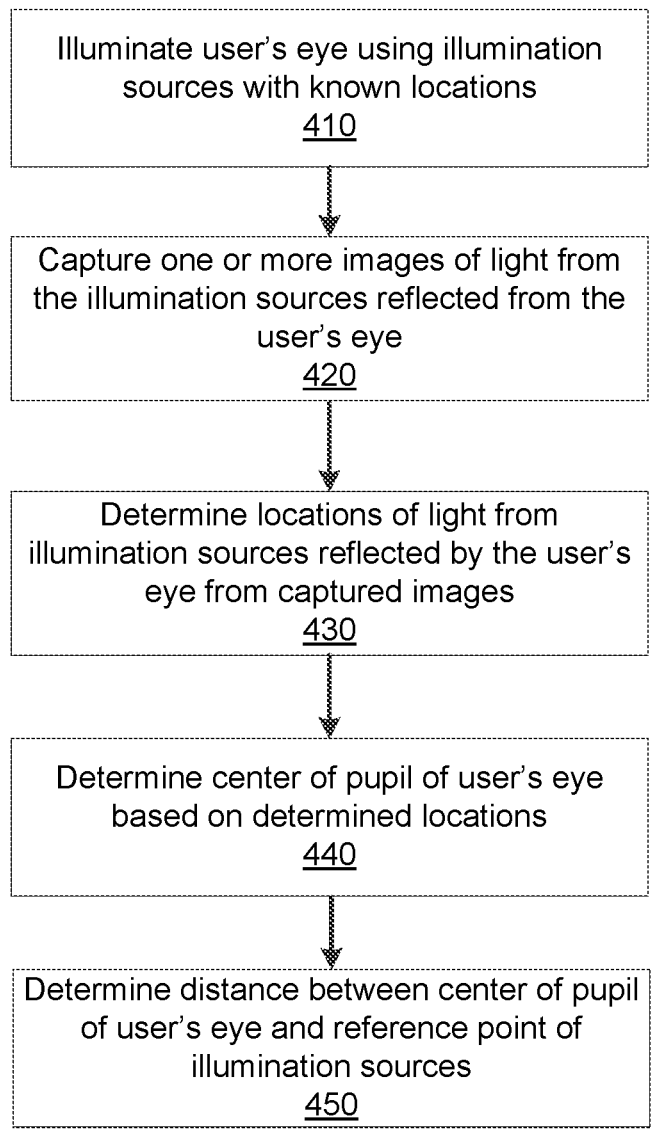
FIG. 4 is a flowchart of an example process for determining interpupillary distance between centers of pupils of a user's eyes, in accordance with an embodiment.

FIG. 4 is a flowchart of one embodiment of a method for determining interpupillary distance between centers of pupils of a user's eyes. In other embodiments, the method may include different or additional steps than those described in conjunction with FIG. 4. Additionally, the method may perform the steps in different orders than the order described in conjunction with FIG. 4 in various embodiments.

In various embodiments, the method described in conjunction with FIG. 4 is a calibration process performed by the VR system environment 100. For example, the VR console 110 communicates one or more instructions to the VR headset 105 to perform the calibration process. During the calibration process, the VR headset 105 may prompt the user to focus the user's eyes on one or more specific locations on the electronic display 115. For example, the electronic display 115 presents an image in a particular location, and prompts the user to focus the user's eyes on the particular location. In some embodiments, the electronic display 115 presents a bright dot in the center of the electronic display 115 and prompts the user to focus the user's eyes on the bright dot.

While the user's eye is focused on the particular location of the electronic display 115, the eye measurement system 160 illuminates 410 the user's eye using the two or more illumination sources 262, 264. As further described above in conjunction with FIG. 3, the illumination sources 262, 264 have specified positions relative to a reference point or relative to each other. For example, multiple illumination sources 262, 264 are positioned to form a circle with its origin at the reference point and having a specified radius. In various embodiments, the illumination sources 262, 264 emit infrared light to illuminate 410 the user's eye.

A portion of the light emitted by the illumination sources 262, 264 is reflected by the user's eye, and an image capture device 266 in the eye measurement system 160 captures 420 one or more images of the reflected light. For example, the cornea of the user's eye reflects light emitted by the illumination sources 262, 264, and the image capture device 266 captures 420 one or more images of the reflected light. In various embodiments, the image capture device 266 is an infrared camera that captures images of infrared light emitted by the illumination sources 262, 264 that is reflected by the user's eye.

From the captured images of the light reflected by the user's eye, the eye measurement system 160 determines 430 locations of light from different illumination sources 262, 264 reflected by the user's eye. For example, the eye measurement system 160 identifies portions of the captured images with greater than a threshold intensity, which the eye measurement system 160 determines 430 as locations of the illumination sources 262, 264. If the illumination sources 262, 264 are positioned to form a circle centered at the reference point and having a particular radius, the eye measurement system 160 determines locations of light reflected by the user's eye by identifying locations of light in the captured images having greater than a threshold intensity, which correspond to positions of the illumination sources 262, 264 emitting the light; hence, the eye measurement system 160 determines 430 a circle of locations of light having greater than the threshold intensity in the captured images.

Based on the determined locations in the captured images, the eye measurement system 160 determines 440 a center of a pupil of the user's eye. For example, if the illumination sources 262, 264 are positioned as circle, the eye measurement system 160 determines 430 a circle of locations of light having greater than the threshold intensity in the captured images and determines 440 the origin of the circle of locations of light as the center of the pupil of the user's eye. In other embodiments where the illumination sources 262, 264 have different orientations relative to each other, the eye measurement system 160 determines the center of the pupil of the user's eye based on the determined locations of light from the illumination sources 262, 264 reflected by the user's eye.

The eye measurement system 160 determines 450 a distance between the determined center of the pupil of the user's eye and a reference point of the illumination sources 262, 264. For example, if the illumination sources 262, 264 are positioned in a circle having an origin at reference point, the eye measurement system 160 determines 450 a distance between the reference point and the center of the pupil of the user's eye, which was determined 440 as the origin of a circle formed by locations of light having greater than the threshold intensity in the captured images. By determining 450 distances between the determined center of the pupil of the user's eye and a reference point of the illumination sources 262, 264 for each eye of the user, the eye measurement system 160 determine an interpupillary distance (IPD) of the user. In one embodiment, the eye measurement system 160 determines the IPD of the user as a sum of the distance between a reference point of illumination sources 262, 264 for an eye of the user and a reference point of illumination sources 262, 264 for another eye of the user, the distance between the determined center of the pupil of the eye of the user and reference point of illumination sources 262, 264 for an eye of the user, and the distance between the determined center of the pupil of the other eye of the user and reference point of illumination sources 262, 264 for the other eye of the user.

In some embodiments, the eye measurement system 160 for a user's eye is horizontally and vertically aligned with a lens in the VR headset 105 corresponding to the user's eye and includes a mechanism to reposition the lens in the VR headset 105 based on the distance between the measured positions of the pupils of the user's eyes and the reference point of the illumination sources 262, 264 for the user's eye. For example, the eye measurement system 160 communicates information to the electronic display 115 to display the determined center of the pupil of the user's eye on the electronic display 115 along with a prompt for the user to reposition the lens in the VR headset 105 so the center of the determined center of the pupil of the user's eye is aligned with the reference point of the illumination sources 262, 264 for the user's eye or is within a threshold distance of the reference point of the illumination sources 262, 264 for the user's eye. Alternatively, the eye measurement system 160 includes one or more motors coupled to the lens in the VR headset 160. The eye measurement system 160 communicates one or more control signals to the one or more motors to reposition the lens in the VR headset 105 based on the distance between the determined center of the pupil of the user's eye and the reference point of the illumination sources 262, 264 for the user's eye. For example, the one or more motors reposition the lens in the VR headset 105 so the center of the determined center of the pupil of the user's eye is aligned with the reference point of the illumination sources 262, 264 for the user's eye or is within a threshold distance of the reference point of the illumination sources 262, 264 for the user's eye.

In various embodiments, the eye measurement system 160 also determines a distance between the user's eye and a surface of a lens in the VR headset 105 based on one or more dimensions of the determined locations of light from the illumination sources 262, 264 in the captured images. For example, the eye measurement system 160 maintains information associating different dimensions of the determined locations of light from the illumination sources 262, 264 in the captured images with different distances between the user's eye and a surface of a lens in the VR headset 105. In various embodiments, each dimension of the determined locations of light from the illumination sources 262, 264 in the captured images corresponds to a distance between the user's eye and a surface of the lens in the VR headset 105. For example, if the illumination sources 262, 264 are positioned in a circle having a specified radius from a reference point, the eye measurement system 160 includes information associating different radii of a circle formed by locations of light from the illumination sources 262, 264 in the captured images with different distances between the user's eye and the surface of the lens in the VR headset 105. Hence, the eye measurement system 160 determines a corresponding distance between the user's eye and the surface of the lens in the VR headset 105 corresponding to a radius of the circle formed by locations of light from the illumination sources 262, 264 in the captured images. In various embodiments, distances between the user's eye and a surface of the lens in the VR headset 105 corresponding to one or more dimensions of the determined locations of light from the illumination sources 262, 264 in the captured images are initially determined through a function based on the one or more dimensions and subsequently stored for retrieval by the eye measurement system 160.

Additional Configuration Information

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. An apparatus comprising:
a plurality of illumination sources configured to emit light having particular wavelengths to illuminate a surface of a user's eye, different illumination sources configured to emit light having specific temporal patterns;
an image capture device configured to capture a plurality of images of light from the plurality of illumination sources reflected by the surface of the user's eye; and
a processor coupled to the image capture device, the processor configured to:
determine locations of light from the plurality of illumination sources reflected by the surface of the user's eye having at least a threshold intensity from the plurality of images,
determine a center of a pupil of the user's eye in three spatial dimensions based on the determined locations, and
determine a distance between the determined center of the pupil of the user's eye and a reference point of the plurality of illumination sources.

2. The apparatus of claim 1, further comprising:
an additional plurality of illumination sources configured to emit light having the particular wavelengths to illuminate a surface of the user's other eye;
an additional image capture device coupled to the processor, the additional image capture device configured to capture additional images of light from the additional plurality of illumination sources reflected by the surface of the user's other eye; and
the processor further configured to:
determine locations of light from the additional plurality of illumination sources reflected by the surface of the user's other eye having at least the threshold intensity from the additional plurality of images,
determine a center of a pupil of the user's other eye based in part on the determined locations of light from the additional plurality of illumination sources reflected by the surface of the user's other eye having at least the threshold intensity, and
determine a distance between the determined center of the pupil of the user's other eye and a reference point of the additional plurality of illumination sources.

3. The apparatus of claim 2, wherein the processor is further configured to:
determine an interpupillary distance between the user's eye and the user's other eye as a sum of a distance between the reference point of the plurality of illumination sources and the reference point of the additional plurality of illumination sources for the user's another eye, the determined distance between the center of the pupil of the user's eye and the reference point of the plurality of illumination sources, and the determined distance between the center of the pupil of the user's other eye and the reference point of the additional plurality of illumination sources.

4. The apparatus of claim 3, wherein the apparatus is a part of a headset.

5. The apparatus of claim 1, wherein the apparatus includes a lens coupled to a motor and positioned proximate to the user's eye and the processor is further configured to:
communicate a control signal to the motor based on the interpupillary distance, the control signal based on the distance between the determined center of the pupil of the user's eye and the reference point of the plurality of illumination sources and causing the motor to reposition the lens so the determined center of the pupil of the user's eye is within a threshold distance of the reference point of the plurality of illumination sources.

6. The apparatus of claim 1, wherein the apparatus includes a lens positioned proximate to the user's eye and the processor is further configured to:
determine a distance between a portion of the user's eye and a surface of the lens based on one or more dimensions of the locations of light from the plurality of illumination sources reflected by the surface of the user's eye.

7. The apparatus of claim 6, wherein determine the distance between the portion of the user's eye and the surface of the lens based one or more dimensions of the locations of light from the plurality of illumination sources reflected by the surface of the user's eye comprises:
maintain information associating different dimensions of locations of light reflected by the surface of the user's eye with different distances between the portion of the user's eye and the surface of the user's eye; and
determine a dimension of the locations of light from the plurality of illumination sources reflected by the surface of the user's eye; and
determine the distance between the portion of the user's eye and the surface of the user's eye as a distance between the portion of the user's eye and the surface of the user's eye corresponding to the determined dimension by the maintained information.

8. The apparatus of claim 7, wherein the dimension of the locations of light from the plurality of location sources reflected by the surface of the user's eye comprises a radius of the locations of light from the plurality of location sources reflected by the surface of the user's eye.

9. The apparatus of claim 1, wherein each of the plurality of illumination sources has a different depth specified position relative to the reference point.

10. The apparatus of claim 1, wherein the plurality of illumination sources forms a circle having a specified radius and an origin at the reference point.

11. The apparatus of claim 1, wherein each of the plurality of illumination sources is positioned outside of the user's line of sight.

12. The apparatus of claim 1, wherein different illumination sources of the plurality of illumination sources have different depths relative to the reference point.

13. The apparatus of claim 1, wherein different illumination sources of the plurality of illumination sources are configured to emit light having different wavelengths.

14. The apparatus of claim 1, wherein the surface of the user's eye is a cornea of the user's eye.

15. The apparatus of claim 1, further comprising:
a hot mirror positioned between an electronic display presenting content to the user's eye and the user's eye, the hot mirror configured to reflect light from emitted from the plurality of illumination sources and reflected by the user's eye towards the image capture device and to not reflect visible light from the electronic display.

16. A method comprising:
illuminating a surface of a user's eye with light emitted by a plurality of illumination sources, different illumination sources configured to emit light having specific temporal patterns;
capturing a plurality of images of light from the plurality of illumination sources reflected by the surface of the user's eye;
determining locations of light emitted by the plurality of illumination sources reflected by the surface of the user's eye having at least a threshold intensity from the plurality of images;
determining a center of a pupil of the user's eye in three spatial dimensions based on the determined locations; and
determining a distance between the determined center of the pupil of the user's eye and a reference point of the plurality of illumination sources.

17. The method of claim 16, further comprising:
determining a distance between a portion of the user's eye and a surface of a lens included in a headset that also includes the plurality of illumination sources based on one or more dimensions of the locations of light from the plurality of illumination sources reflected by the surface of the user's eye.

18. The method of claim 16, further comprising:
illuminating a surface of the user's other eye with light emitted by an additional plurality of illumination sources;
capturing an additional plurality of images of light from the plurality of illumination sources reflected by the surface of the user's other eye;
determining locations of light emitted by the additional plurality of illumination sources reflected by the surface of the user's other eye having at least the threshold intensity from the additional plurality of images;
determining a center of a pupil of the user's other eye based on the determined locations of light emitted by the additional plurality of illumination sources reflected by the surface of the user's other eye having at least the threshold intensity from the additional plurality of images; and
determining an additional distance between the determined center of the pupil of the user's other eye and a reference point of the additional plurality of illumination sources.

19. The apparatus of claim 18, wherein determining the distance between the portion of the user's eye and the surface of the lens included in the headset that also includes the plurality of illumination sources based one or more dimensions of the locations of light from the plurality of illumination sources reflected by the surface of the user's eye comprises:
maintaining information associating different dimensions of locations of light reflected by the surface of the user's eye with different distances between the portion of the user's eye and the surface of the user's eye; and
determining a dimension of the locations of light from the plurality of illumination sources reflected by the surface of the user's eye; and
determining the distance between the portion of the user's eye and the surface of the user's eye as a distance between the portion of the user's eye and the surface of the user's eye corresponding to the determined dimension by the maintained information.

20. The method of claim 18, further comprising:
determining an interpupillary distance between the user's eye and the user's other eye as a sum of a distance between the reference point of the plurality of illumination sources and the reference point of the additional plurality of illumination sources for the user's another eye, the determined distance between the center of the pupil of the user's eye and the reference point of the plurality of illumination sources, and the determined distance between the center of the pupil of the user's other eye and the reference point of the additional plurality of illumination sources.

21. The method of claim 16, further comprising:
repositioning a lens included in a headset including the plurality of illumination sources based on the distance between the determined center of the pupil of the user's eye and the reference point of the plurality of illumination sources.

* * * * *

UNITED STATES PATENT AND TRADEMARK OFFICE
CERTIFICATE OF CORRECTION

PATENT NO. : 10,401,625 B2
APPLICATION NO. : 15/391204
DATED : September 3, 2019
INVENTOR(S) : Yury Anatolievich Petrov Page 1 of 1

It is certified that error appears in the above-identified patent and that said Letters Patent is hereby corrected as shown below:

In the Claims

In Column 14, Claim 7, Line 42, delete "based" and insert -- based on --, therefor.

In Column 15, Claim 11, Line 2, delete "sources is" and -- sources are --, therefor.

In Column 15, Claim 15, Line 13, delete "user's eye" and insert -- user's other eye --, therefor.

Signed and Sealed this
Twenty-third Day of June, 2020

Andrei Iancu
*Director of the United States Patent and Trademark Office*